United States Patent [19]
Ackrell

[11] 4,066,663
[45] Jan. 3, 1978

[54] 6,11-DIHYDRODIBENZO-[B.E.]-THIEPIN-11-ONE-3-ALDEHYDE AND 3-ACETAL DERIVATIVES

[75] Inventor: Jack Ackrell, Palo Alto, Calif.

[73] Assignee: Syntex (U.S.A.) Inc., Palo Alto, Calif.

[21] Appl. No.: 701,780

[22] Filed: July 1, 1976

[51] Int. Cl.$^2$ ............................................ C07D 337/12
[52] U.S. Cl. ................................................. 260/327 B
[58] Field of Search ...................... 260/327 B, 240 R

[56] References Cited
U.S. PATENT DOCUMENTS 3,946,036  3/1976  Gadient ............................. 260/327 B

OTHER PUBLICATIONS

Coates et al., Synthetic Methods of Organic Chemistry, vol. 25, No. 185 (1971).
Novikov et al., Synthetic Methods of Organic Chemistry, vol. 17, No. 202 (1963).

*Primary Examiner*—Cecilia M. S. Jaisle
*Attorney, Agent, or Firm*—Gerard A. Blaufarb; William B. Walker

[57] ABSTRACT

The novel compounds 6,11-dihydrodibenzo[b.e.]-thiepin-11-one-3-acetaldehyde and (dl) 2(6,11-dihydrodibenzo-[b.e.]-thiepin-11-one-3-yl)propionaldehyde, certain dialkyl- and cyclic acetals thereof, and processes and novel intermediates for making same.

18 Claims, No Drawings

6,11-DIHYDRODIBENZO-[B.E.]-THIEPIN-11-ONE-3-ALDEHYDE AND 3-ACETAL DERIVATIVES

This invention relates to novel 6,11-dihydrodibenzo-[b.e.]-thiepin-11-one derivatives represented by the formulas

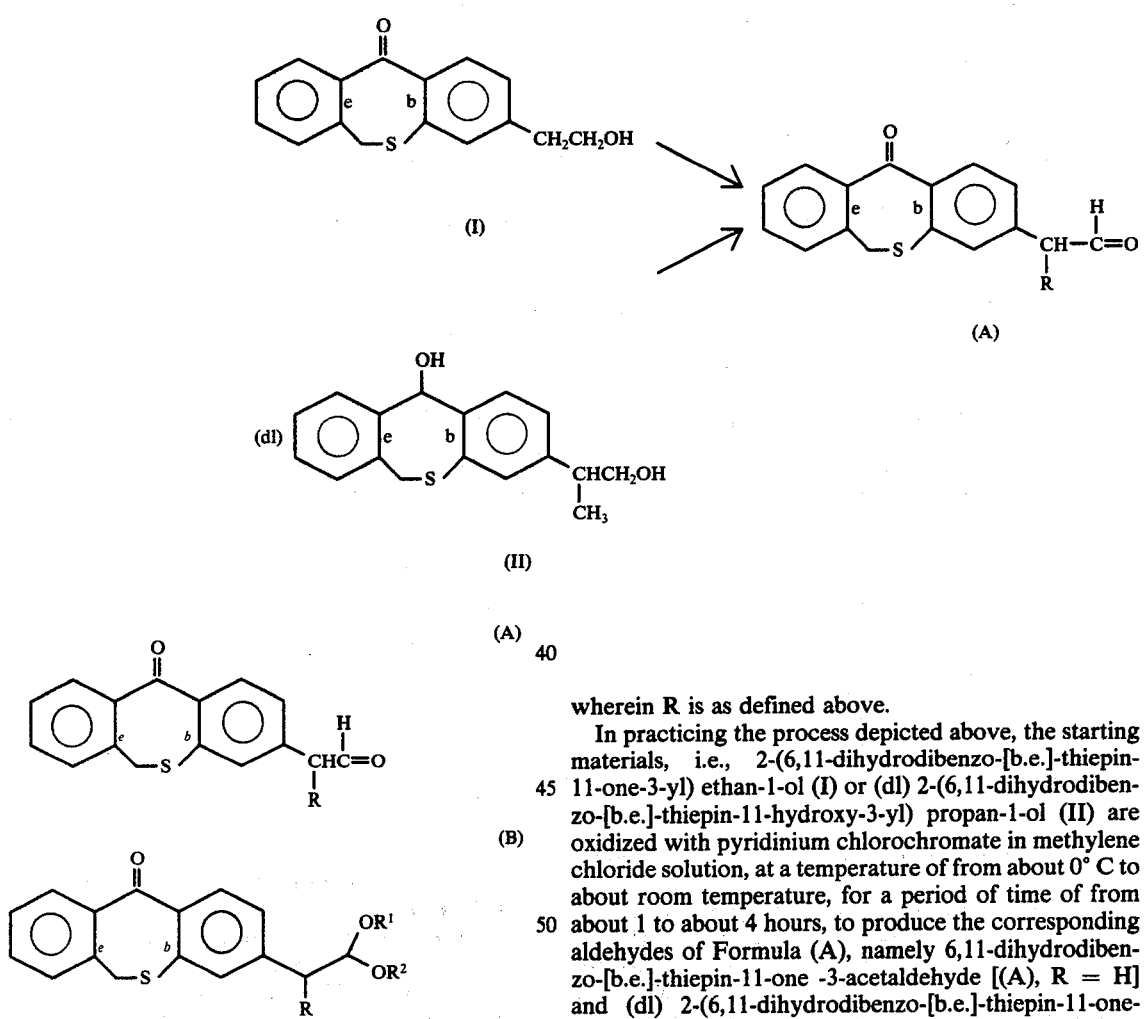

wherein R represents hydrogen or methyl; and each $R^1$ and $R^2$, which can be the same or different, represents a lower alkyl group of 1 to 6 carbon atoms, or together represent a lower alkylene radical of 2 to 6 carbon atoms, to the process for the production thereof and to novel intermediates obtained in the preparation of the compounds of Formula (B).

The compounds of the present invention in which R is methyl possess as asymmetric center and thus exist as pairs of enantiomorphs (optical isomers) i.e., as (dl) mixtures. The compounds of Formula (B) in which R is methyl and $R^1$ and $R^2$ are different possess two asymmetric centers and thus exist as pairs of diasteroisomers and each diasteroisomeric isomer is a (dl) mixture.

As used herein, the term "lower alkyl" refers to alkyl groups of straight chain containing from 1 to 6 carbon atoms. Typical alkyl groups include methyl, ethyl, n-propyl, n-butyl, n-pentyl and n-hexyl.

The term "lower alkylene" refers to both straight and branched alkylene radicals containing from 2 to 6 carbon atoms, e.g., ethylene, propylene, 1,1-dimethylpropylene, 2,3-dimethylbutylene and the like.

The novel compounds of Formula (A) can be prepared by a process illustrated by the following equation:

wherein R is as defined above.

In practicing the process depicted above, the starting materials, i.e., 2-(6,11-dihydrodibenzo-[b.e.]-thiepin-11-one-3-yl) ethan-1-ol (I) or (dl) 2-(6,11-dihydrodibenzo-[b.e.]-thiepin-11-hydroxy-3-yl) propan-1-ol (II) are oxidized with pyridinium chlorochromate in methylene chloride solution, at a temperature of from about 0° C to about room temperature, for a period of time of from about 1 to about 4 hours, to produce the corresponding aldehydes of Formula (A), namely 6,11-dihydrodibenzo-[b.e.]-thiepin-11-one -3-acetaldehyde [(A), R = H] and (dl) 2-(6,11-dihydrodibenzo-[b.e.]-thiepin-11-one-3-yl) propionaldehyde [(A), R = $CH_3$]. There are used from 1 to 3 molar equivalents of the oxidizing agent per hydroxyl group in the starting compound.

Alternative oxidizing agents that can be employed and chromium trixoide-pyridine complex, chromium trioxoide-dipyridine complex (Collins reagent) and Jones reagent.

The starting materials of Formulas (I) and (II) can be prepared as described in my copending patent application Ser. No. 604,291, filed Aug. 13, 1975 now U.S. Pat. No. 3,989,839 which is hereby incorporated by reference, and made a part hereof.

The acetal derivatives represented by Formula (B) above, can be prepared in accordance with the process illustrated by the following reaction scheme:

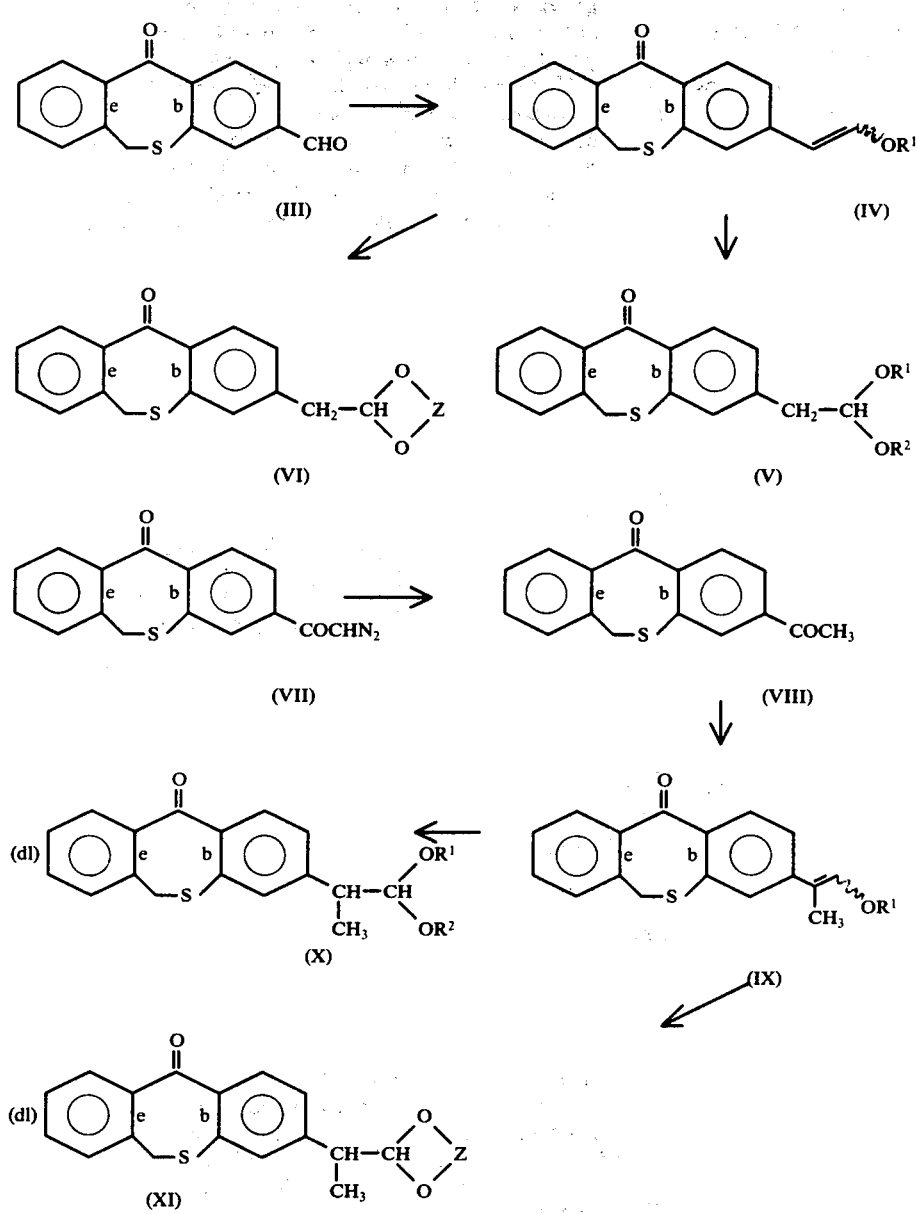

wherein each R[1] and R[2] is lower alkyl and Z is lower alkylene.

In practicing the process depicted above, 6,11-dihydrodibenzo-[b.e.]-thiepin-11-one-3-aldehyde (III) is treated with 1 to 1.5 molar equivalents of an alkoxyalkyltriphenylphosphonium halide in the presence of potassium t-butoxide in a suitable inert organic solvent, to produce the enol ethers of Formula (IV), as a mixture of cis and trans isomers. This reaction is preferably effected under anhydrous conditions, in an inert atmosphere, i.e., under argon or nitrogen atmosphere, at a temperature of from about −15° to about 5° C, for a period of time of from about 5 minutes to about 2 hours. Suitable solvents for this reaction are the ethereal solvents such as tetrahydrofuran, dimethoxyethane, dioxane, diethyl ether and the like. Examples of suitable phosphonium halide reagents are methoxymethyltriphenylphoshonium chloride, ethoxymethyltriphenylphosphonium bromide, n-propoxymethyltriphenylphosphonium chloride, n-hexyloxymethyltriphenylphosphonium chloride and the like.

By reaction of the enol ethers of Formula (IV) with an aliphatic alcohol of 1 to 6 carbon atoms, i.e., methanol, ethanol, propanol, n-butanol, n-pentanol and n-hexanol, there is obtained the corresponding dialkyl acetal of Formula (V). This reaction is conducted in the presence of a strong organic or inorganic acid as catalyst, e.g., perchloric acid, sulfuric acid, p-toluenesulfonic acid, trifluoroacetic acid and the like, at reflux temperature for from about 1 to about 24 hours. The preferred catalyst is perchloric acid.

The alcohol may serve both as reagent and solvent, or alternatively, the reaction can be conducted in the presence of a cosolvent, using particularly an aromatic hydrocarbon such as benzene, toluene or xylene as the cosolvent.

The alkoxy groups in the acetal compounds of Formula (V) can be the same or different. Thus when the alcohol used in this reaction is the alcohol corresponding to the meaning of the R[1] group in the starting enol ether (IV), the R[1] and R[2] groups in the acetal will be the same, while when using a different alcohol there will be obtained mixed acetals.

By treatment of 3-(2-methoxy)vinyl-6,11-dihydrodibenzo-[b.e.]-thiepin-11-one (IV, R¹ = Me) with a glycol containing from 2 to 6 carbon atoms in an inert organic solvent such as a hydrocarbon or ether solvent, and in the presence of an acid catalyst of the type previously mentioned, at reflux temperature for from about 1 to about 4 hours there are obtained the cyclic acetals of Formula (VI). Examples of suitable glycols are: ethylene glycol, propylene glycol, 2,2-dimethylpropylene glycol and 2,3-dimethylbutane-1,4-diol. The reaction is preferably conducted in diemthoxyethane solution using perchloric acid as catalyst.

By treatment of 3-diazoacetyl-6,11-dihydrodibenzo-[b.e.]-thiepin-11-one (VII) with hydroiodic acid in a suitable inert organic solvent, there is obtained 3-acetyl-6,11-dihydrodibenzo-[b.e.]-thiepin-11-one (VIII). This reaction is effected at a temperature of from about 0° to about 30° C, preferably at room temperature, for from about 30 minutes to about 4 hours, using from about 2 to about 10 molar equivalents of hydroiodic acid per mol of starting compound.

In the preferred embodiments the reaction is conducted at room temperature for about 1 hour, using chloroform as solvent.

Upon reaction of the acetyl compound of Formula (VIII) with an alkoxymethyltriphenylphosphonium halide in the presence of potassium t-butoxide there is obtained the corresponding enol ether of Formula (IX), as a mixture of cis and trans isomers. This reaction is preferably effected by mixing initially the starting compound (VIII) with from about 1.1 to about 1.5 molar equivalents of the alkoxymethyltriphenylphosphonium halide in an anhydrous ethereal solvent, e.g., dimethoxyethane, cooling the mixture to about 0° C and adding thereto a solution of from about 1.1 to about 1.5 molar equivalents of potassium t-butoxide in t-butanol, maintaining the reaction mixture at room temperature for from about 5 to about 30 minutes. Examples of suitable alkoxymethyltriphenylphosphonium halides are methoxymethyltriphenylphosphonium chloride, ethoxymethyltriphenylphosphonium bromide, n-propoxymethyltriphenylphosphonium bromide and n-hexyloxymethyltriphenylphosphonium chloride.

By reaction of the enol ethers of Formula (IX) with an aliphatic alcohol of 1 to 6 carbon atoms, in the presence of an acid catalyst of the type previously mentioned, as described hereinbefore in detail for the transformation of (IV) into (V), there are obtained the corresponding racemic dialkyl acetals of Formula (X).

The racemic cyclic acetals of Formula (XI) are obtained by treatment of 3-(2-methoxy-1-methyl)vinyl-6,11-dihydrodibenzo-[b.e.]-thiepin-11-one (IX, R¹ = Me) with a glycol containing from 2 to 6 carbon atoms, in the presence of an acid catalyst of the type previously mentioned, using particularly perchloric acid. The reaction is preferably conducted in an aromatic hydrocarbon solvent e.g., benzene, toluene and xylene, at the reflux temperature of the reaction mixture, distilling off part of the solvent to eliminate moisture, for a period of time of from about 15 minutes to about 2 hours.

The starting compounds of Formulas (III) and (VII) can be prepared in accordance with copending applications Ser. No. 697,648, filed June 18, 1976, and Ser. No. 634,086, filed Nov. 21, 1975, now U.S. Pat. No. 4,000,308, respectively, which are hereby incorporated by reference and made a part hereof.

The novel intermediates in the obtention of the dialkyl acetals and cyclic acetals of Formula (B) are represented by the formula

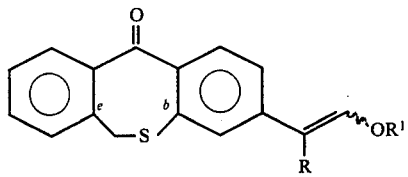

(C)

wherein R and R¹ have the above-indicated meaning, which is a composite of Formulas (IV) and (IX) above.

In each of the process steps, described herein above and below, unless otherewise indicated, the respective intermediate products are preferably separated from the reaction mixture and purified prior to their use as starting materials for the next step in the process. Such separation and purification can be effected by any suitable procedure. For example, typical separation procedures include filtration, extraction, evaporation, and typical purification procedures include crystallization, and both thin-layer and column chromatography. Optimum separation and isolation procedures can be obtained for any given step by routine experimentation as will be apparent to those skilled in this art.

The compound of Formulas (A) and (B) are useful as anti-inflammatory agents, analgetic agents, platelet aggregation inhibitors, fibrinolytic agents, and as smooth muscle relaxants. The compounds of Formulas (A) and (B) can be used both prophylactically and therapeutically.

The compounds of Formulas (A) and (B) exhibit anti-inflammatory, analgesic and anti-pyretic activities. Accordingly, the compositions containing these compounds are useful in the treatment and elimination of inflammation such as inflammatory conditions of the muscular skeletal system, skeletal joints and other tissues, for example, in the treatment of inflammatory conditions such as rheumatism, concussion, laceration, arthritis, bone fractures, post-traumatic conditions, and gout. In those cases in which the above conditions include pain and pyrexia coupled with inflammation, the instant compounds are useful for the relief of these conditions as well as the inflammation.

Administration of the active compound of Formulas (A) and (B) in an appropriate pharmaceutical composition can be via any of the accepted modes of administration of agents for the treatment of inflammation, pain, or pyrexia, or the prophylaxis thereof. Thus, administration can be for example, orally, parenterally, or topically, in the form of solid, semi-solid or liquid dosage forms, such as, for example, tablets, suppositories, pills, capsules, powders, liquids, suspensions, creams, lotions, ointments, or the like, preferably in unit dosage forms suitable for simple administration of precise dosages. The compositions will include a conventional pharmaceutical carrier or excipient and an active compound of Formulas (A) and (B), and, in addition, may include other medicinal agents, pharmaceutical agents, carriers, adjuvants, etc.

The preferred manner of administration, for the conditions detailed above, is oral using a convenient daily dosage regimen which can be adjusted according to the degree of afflication. Generally, a daily dose of from 0.1 mg. to 50 mg. of the active compound of Formulas (A)

and (B) per kilogram of body weight is used. Most conditions respond to treatment comprising a dosage level of the order of 0.5 mg. to 15 mg. per kilogram of body weight per day. For such oral administration, a pharmaceutically acceptable non-toxic composition is formed by the incorporation of any of the normally employed excipients, such as, for example, pharmaceutical grades of mannitol, lactose, starch, magnesium stearate, sodium saccharin, talcum, cellulose, glucose, sucrose, magnesium carbonate, and the like. Such compositions take the form of solution, suspensions, tablets, pills, capsules, powders, sustained release formulations and the like.

The active compounds of Formulas (A) and (B) may be formulated into a suppository using, for example, polyalkylene glycols, for example, polypropylene glycol, as the carrier. Liquid pharmaceutically administerable compositions can, for example, be prepared by dissolving, dispersing, etc., an active compound of Formulas (A) and (B) and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of non-toxic auxiliary substances such as wetting or emusifying agents, pH buffering agents and the like, such as for example, sodium acetate, sorbitan monolaurate, triethanolamine oleate, etc.

Actual methods of preparing such dosage forms are known, or will be apparent, to those skilled in this art; for example, see Remington's Pharmaceutical Sciences, Mack Publishing Company, Easton, PA, 14th Edition, 1970. The composition to be administered will, in any event, contain a quantity of the active compound(s) in a pharmaceutically effective amount for relief of the particular condition being treated in accordance with the teachings of this invention.

The compounds of Formulas (A) and (B) described above are also uterine smooth muscle relaxants and thus are useful as agents for maintaining the pregnancy of pregnant mammals, for the benefit of the mother and/or the fetus, until termination of the pregnancy is considered, from a medical point of view, to be favorable, or more favorable, for the mother and/or the fetus. It should be understood, however, that in certain instances, for example where parturition has already begun (i.e., the mother is experiencing uterine contractions, especially near full term), that administration of the compounds herein described may not maintain the pregnant state for an indefinite period of time. Rather, in such instances, the pregnancy will, most probably, be slightly "prolonged," a factor which may be advantageous to either the mother and/or the fetus.

In particular, the compounds of Formulas (A) and (B) are used as agents for delaying the onset of, or for postponing, parturition. As used in this application, the phrase "to delay the onset of parturition" is intended to cover that delay in parturition caused by the administration of the compounds of Formula(s) (A) and (B) at any time. before uterine muscle contractions have begun. Thus, it is intended that the aforementioned phrase cover abortion prevention early in pregnancy (i.e., before the fetus is "viable") as well as delaying premature parturition, a term which sometimes is used with reference to that premature labore experienced later in the pregnancy when the fetus is considered to be "viable." In either case, the agents are administered as prophylactic agents in that such administration tends to prevent the onset of parturition. This administration is particularly useful in the treatment of women having a history of spontaneous abortion, miscarriage or premature delivery (i.e., delivery prior to full term). Such administration is also useful where there are clinical indications that the pregnancy might be terminated prior to that time and is considered favorable to the mother and/or fetus.

With respect to animals, this treatment can also be utilized to synchronize the deliveries from a group of pregnant animals to happen at or about the same time, or to happen at or about a desired time and/or place, when the births can be handled with greater facility.

As used in this application, the phrase "postponing parturition" is intended to cover that delay in parturition caused by the administration of the compounds of Formulas (A) and (B) after uterine muscle contractions have begun. The condition of the patient, including the time within the gestation period when the contractions have begun, the severity of the contractions and how long the contractions have taken place will affect the results achieved with the administration of the compounds of Formulas (A) and (B). For example, the effect can be to reduce the intensity and/or the duration of the contractions (the actual act of parturition being "prolonged"), or to stop the contractions altogether. In either case, the effect will be to prolong the gestation period although, depending upon the condition of the patient as described above, the effect may either be slight or, under appropriate circumstances, somewhat greater. Such administration may be to prevent spontaneous abortion, to cause the delivery to be more easily accomplished and/or less painful to the mother, or to occur at a more appropriate time and/or place.

In all cases, administration of the compounds of Formulas (A) and (B), for the purposes set forth herein, should be consistent with best and/or accepted medical (or veterinary) practices so as to maximize the benefits to the mother and the fetus. For example, administration should not be continued so long past full term that the fetus dies in utero.

In the practice of the methods of the present invention, a therapeutically effective amount of a compound of Formulas (A) and (B), or a pharmaceutical composition containing a compound of Formulas (A) and (B), is administered to the pregnant mammal via any of the usual and acceptable methods known in the art. The compound can be administered either singly or in combination with another compound or compounds, as defined above, or other pharmaceutical agents, carriers, adjuvants, etc. Such compound(s) or compositions can be administered orally, parenterally, either in the form of solid, semi-solid, or liquid dosage forms, Typically, administration is by a pharmaceutical composition containing the pharmaceutically active compound and one or more pharmaceutical carriers or adjuvants.

The administerable pharmaceutical composition may take the form of oral tablets, vaginal or uterine tablets or suppositories, pills, capsules, liquid solutions, suspensions, or the like, preferably in unit dosage forms suitable for simple administration of precise dosages. Conventional non-toxic solid carriers include, for example, pharmaceutical grades of mannitol, lactose, starch, magnesium stearate, sodium saccharin, talcum, cellulose, glucose, sucrose, magnesium carbonate, and the like. The active compound as defined above may be formulated as suppositories using, for example, polyalkylene glycols, for example, polypropylene glycol, as the carrier. Liquid pharmaceutically administerable compositions can, for example, be prepared by dissolving, dispersing, etc. an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of non-toxic auxiliary substances such as wetting or emusifying agents, pH buffering agents and the like, for example, sodium acetate, sorbitan monolaurate, triethanolamine oleate, etc. Actual methods of preparing such dosage forms are known, or will be apparent, to those skilled in this art; for example, see Remington's Pharmaceutical Sciences, Mack Publishing Company, Easton, Pa., 14th. Edition, 1970. The composition or formulation to be administered will, in any event, contain a quantity of the active compound(s) in an amount effective to delay the onset of parturition or to postpone parturition if uterine contractions have already begun. Generally a daily dose of from about 10 mg. to about 250 mg. of the active compound per kilogram of body weight will be administered, with administration being a single daily dose or up to three or four smaller doses regularly given throughout the day. The amount of active compound administered will, of course depend on its relative activity.

The following Examples illustrate the invention but are not intended to limit its scope. When necessary examples are repeated to provide additional material for subsequent examples. All mixture ratios used with regard to liquids refer to volume ratios. By the term "room temperature" is meant from about 20° to about 25° C.

EXAMPLE 1

A solution of 200 mg. of 2-(6,11-dihydrodibenzo-[b.e.]-thiepin-11-one-3-yl)ethan-1-ol (I) in 2 ml. of methylene chloride is added to a stirred solution of 260 mg. of pyridinium chlorochromate in 20 ml. of methylene chloride. The reaction mixture is maintained at room temperature for 2 hours, 20 ml. of hexane is then added and the resulting mixture is filtered through 5 g. of Florisil, eluting with methylene chloride:hexane (1:1). Evaporation of the combined eluates affords 30 mg. of 6,11-dihydrodibenzo-[b.e.]-thiepin-11-one-3-acetaldehyde [(A), R = H], an amorphous solid, having the following physical constants: U.V.: $\lambda_{max}^{Diox}$ 250, 280, 350 nm ($\epsilon$ 19100; 8300, 2700); I.R.: $\nu_{max}^{CHCl_3}$ 1745, 1640, 1600 cm$^{-1}$; N.M.R.: $\delta_{TMS}^{CDCl_3}$ 3.60 (d, 2H), 3.98 (s, 2H), 6.83-7.60 (m, 6H), 8.10 (d, 1H), 9.60 ppm. (d, 1H); M.S.: m/e 268 (M+).

EXAMPLE 2

A solution of 2 g. of 6,11-dihydrodibenzo-[b.e.]-thiepin-11-one-3-aldehyde (III) in 10 ml. of dry tetrahydrofuran is added slowly, with stirring, to a mixture of 1.3 g. of methoxymethyltriphenylphosphonium chloride, 1.3 g. of potassium t-butoxide and 20 ml. of t-butanol cooled to −10° C. After 1 hour the reaction is quenched by adding 10 ml. of saturated sodium chloride solution. The resultant mixture is diluted with 100 ml. of water and extracted with ethyl acetate (2 × 30 ml.). The combined extracts are dried over sodium sulfate and decolorized with charcoal. Evaporation of the solvent affords the crude 3-(2-methoxy)vinyl-6,11-dihydrodibenzo-[b.e.]-thiepin-11-one (IV, R$^1$ = Me, mixture of cis and trans isomers) as an oil, which is purified by chromatography on 40 g. of Florisil using hexane: ethyl acetate (1:8) as eluant. The combined eluates are evaporated to dryness under reduced pressure and the residue crystallized from ethyl acetate-hexane, at −5° C to yield pure 3-(2-methoxy)vinyl-6,11-dihydrodibenzo-[b.e.]-thiepin-11-one, m.p. 68°-70° C.

In similar manner substituting ethoxymethyltriphenylphosphoniumbromide and n-propoxymethyltriphenylphosphonium chloride for methoxymethyltriphenylphosphonium chloride there are obtained 3-(2-ethoxy)vinyl-6,11-dihydrodibenzo-[b.e.]-thiepin-11-one and 3-(2-n-propoxy)vinyl-6,11-dihydrodibenzo-[b.e.]-thiepin-11-one, respectively.

EXAMPLE 3

A solution of 1.2 g. of 3-(2-methoxy)vinyl-6,11-dihydrodibenzo-[b.e.]-thiepin-11-one (IV, R$^1$ = Me) in 90 ml. of dry methanol containing one drop of 70% aqueous perchloric acid is refluxed for 24 hours. The reaction mixture is cooled and evaporated to dryness under reduced pressure and the residue is chromatographed on 50 g. of silica gel using ethyl acetate:hexane (1:9) as eluant. The combined fractions are evaporated to dryness and the residue crystallized from hexane, to yield 1.2 g. of 3-(2,2-dimethoxy)ethyl-6,11-dihydrodibenzo-[b.e.]-thiepin-11-one (V, R$^1$ and R$^2$ = Me), m.p. 71°-72° C.

In a similar manner, using 3-(2-ethoxy)vinyl-6,11-dihydrodibenzo-[b.e.]-thiepin-11-one and 3-(2-n-propoxy)vinyl-6,11-dihydrodibenzo-[b.e.]-thiepin-11-one as starting materials there are obtained (dl) 3-(2-ethoxy-2-methoxy)ethyl-6,11-dihydrodibenzo-[b.e.]-thiepin-11-one and (dl) 3-(2-methoxy-2-n-propoxy)ethyl-6,11-dihydrodibenzo-[b.e.]-thiepin-11-one, as pairs of diasteroisomers.

EXAMPLE 4

A solution of 1 g. of 3-(2-ethoxy)vinyl-6,11-dihydrodibenzo-[b.e.]-thiepin-11-one in 70 m. of anhydrous ethanol containing one drop of 70% aqueous perchloric acid is refluxed for 18 hours. It is then evaporated to dryness and the residue purified by chromatography on silica gel, to produce 3-(2,2-diethoxy)ethyl-6,11-dihydrodibenzo-[b.e.]-thiepin-11-one.

In a similar manner, starting from 3-(2-n-propoxy)vinyl-6,11-dihydrodibenzo-[b.e.]-thiepin-11-one and using n-propanol as reagent there is obtained 3-(2,2-di-n-propoxy)ethyl-6,11-dihydrodibenzo-[b.e.]-thiepin-11-one.

EXAMPLE 5

A. A solution of 13.5 g. of triphenylphosphine and 7.5 g. of chloromethyl-n-hexyl ether in 50 ml. of toluene is refluxed for 2 hours. The reaction mixture is cooled to room temperature and the crystalline phosphonium salt is filtered off, washed with a little toluene, then with ether, and dried at 90° C, thus obtaining 10 g. of n-hexyloxymethyltriphenylphosphonium chloride, m.p. 150°-154° C.

In a similar manner, substituting chloromethyl n-butyl ether and chloromethyl n-pentyl ether for chloromethyl n-hexyl ether there are obtained n-butyloxymethyltriphenylphosphonium chloride and n-pentyloxymethyltriphenylphosphonium chloride, respectively.

B. A stirred mixture of 1.4 g. of 6,11-dihydrodibenzo-[b.e.]-thiepin-11-one-3-aldehyde (III), 2.25 g. of n-hexyloxymethyltriphenylphosphonium chloride and 30 ml.

of dry dimethoxyethane is cooled to 0° C under a nitrogen atmosphere, and treated with 7.3 ml. of a solution of potassium t-butoxide (prepared from 0.25 g. of potassium and 10 ml. of t-butanol). After 10 minutes the reaction mixture is quenched with 5 ml. of 10% aqueous ammonium chloride, diluted with 100 ml. of water and extracted with benzene (2 × 50 ml.). The organic layers are combined and washed with water (3 × 50 ml.), dried over sodium sulfate and evaporated to dryness. The oily residue is chromatographed on 25 g. of silica gel, eluting with ether:hexane (1:6), to produce 900 mg. of 3-(2-n-hexyloxy)vinyl-6,11-dihydrodibenzo-[b.e.]-thiepin-11-one (IV, $R^1$ = $n$-$C_6H_{13}$, mixture of cis and trans isomers) as a pale yellow oil having the following physical constants: U.V.: $\lambda_{max}^{MeOH}$ 245,333 nm ($\epsilon$ 26,200, 19,500); I.R.: $\nu_{max}^{CHCl_3}$ 1640, 1590 cm$^{-1}$; N.M.R.: $\delta_{TMS}^{CDCl_3}$ 0.70–1.10 (m, 3H), 1.10–2.00 (m, 8H), 3.85 (t,2H), 3.93 (s, 2H), [5.02 (d), 5.63 (d), 6.20 (d), 6.85–8.20 (m),] 9H; M.S.: m/e 352 (M+).

In a similar manner, substituting n-butyloxymethyltriphenylphosphonium chloride and n-pentyloxymethyltriphenylphosphonium chloride for n-hexyloxymethyltriphenylphosphonium chloride there are obtained 3-(2-n-butyloxy)vinyl-6,11-dihydrodibenzo-[b.e.]-thiepin-11-one and 3-(2-n-pentyloxy)vinyl-6,11-dihydrodibenzo-[b.e.]-thiepin-11-one, respectively.

EXAMPLE 6

750 Mg. of 3-(2-n-hexyloxy)vinyl-6,11-dihydrodibenzo- [b.e.]-thiepin-11-one and 2 ml. of n-hexanol are dissolved in 50 ml. of toluene and then 10 ml. of toluene is removed by distillation in order to dry the reaction mixture. Two drops of a solution of 70% perchloric acid in 0.3 ml. of dry dimethoxyethane is added and the mixture is refluxed under nitrogen for 2 hours. The mixture is cooled to room temperature, quenched by adding 2 drops of triethylamine, and evaporated to dryness. The oily residue is chromatographed on 50 g. of silica gel eluting with hexane-ethyl acetate (20:1), to give 805 mg. of 3-(2,2-di-n-hexyloxy)ethyl-6,11-dihydrodibenzo-[b.e.]-thiepin-11-one (V, $R^1$ and $R^2$ = $n$-$C_6H_{13}$), as a pale yellow oil, which has the following physical constants: U.V.: $\lambda_{max}^{MeOH}$ 250, 280, 349 nm ($\epsilon$21,800, 9,900, 4,200); I.R.: $\nu_{max}^{CHCl_3}$ 1640, 1600 cm$^{-1}$; N.M.R.: $\delta_{TMS}^{CDCl_3}$ 0.50–1.70 (b.m., 22H), 2.80 (d, 2H), 3.10–3.70 (b.m., 4H), 3.95 (s, 2H), 4.48 (t, 1H), 6.85–7.50 (m, 6H), 7.99 ppm (d, 1H); M.S.: m/e 454 (M+).

EXAMPLE 7

By following the method of Example 6, using 3-(2-n-butyloxy)vinyl-6,11-dihydrodibenzo-[b.e.]-thiepin-11-one as starting material and n-butanol as reagent there is obtained 3-(2,2-di-n-butyloxy)ethyl-6,11-dihydrodibenzo-[b.e.]-thiepin-11-one.

Similarly, starting from 3-(2-n-pentyloxy)vinyl-6,11-dihydrodibenzo-[b.e.]-thiepin-11-one, using n-pentanol as reagent there is obtained 3-(2,2-di-n-pentyloxy)ethyl-6,11-dihydrodibenzo-[b.e.]-thiepin-11-one.

EXAMPLE 8

A solution of 550 mg. of crude 3-(2-methoxy)vinyl-6,11-dihydrodibenzo-[b.e.]-thiepin-11-one (IV, $R^1$ = Me) in 20 ml. of dry dimethoxyethane containing 1.5 ml. of ethylene glycol and 5 drops of 70% perchloric acid, is refluxed for 2 hours. The reaction mixture is then poured into 100 ml. of water and extracted with ether (3 × 50 ml.). The combined extracts are washed with water (2 × 50 ml.), dried over sodium sulfate and evaporated to dryness. The residue is crystallized from hexane-ether to yield 500 mg. of 2-[(6,11-dihydrodibenzo-[b.e.]-thiepin-11-one-3-yl) methyl]-1,3-dioxolane (VI, Z = —$CH_2$13 $CH_2$—), m.p. 118°–119° C.

In a similar manner, substituting propylene glycol, 2,2-dimethylpropylene glycol and 2,3-dimethylbutane-1,4-diol for ethylene glycol in the above procedure there are respectively obtained: 6,11-dihydrodibenzo-[b.e.]-thiepin-11-one-3-acetaldehyde propylene acetal, 6,11-dihydrodibenzo-[b.e.]-thiepin-11-one-3-acetaldehyde 2,2-dimethylpropylene acetal and 6,11-dihydrodibenzo-[b.e.]-thiepin-11-one-3-acetaldehyde 2,3-dimethylbutylene acetal.

EXAMPLE 9

A stirred solution of 330 mg. of (dl) 2-(6,11-dihydrodibenzo-[b.e.]-thiepin-11-hydroxy-3-yl)propanl-ol (II) in 50 ml. of methylene chloride is treated under an atmosphere of nitrogen with 800 mg. of pyridinium chlorochromate. The reaction mixture is maintained for 100 minutes at room temperature, and then it is poured into 100 ml. of ether, and filtered through a bed of magnesium sulfate. The solid material is thoroughly washed with methylene chloride and the combined filtrates are evaporated to dryness under reduced pressure. The oily residue is chromatographed on 10 g. of silica gel, eluting with hexane:ethyl acetate (4:1). Evaporation of the eluate yields 101 mg. of (dl) 2-(6,11-dihydrodibenzo-[b.e.]-thiepin-11-one-3-yl)propionaldehyde [(A), R = Me], as a pale yellow brown oil, which has the following physical constants: U.V.:$\lambda_{max}^{MeOH}$ 250, 280, 353 nm ($\epsilon$21,400, 10,000, 2,600); I.R.:$\nu_{max}^{CHCl_3}$ 2810, 2710, 1730, 1640, 1595 cm$^{-1}$; N.M.R.:$\delta_{TMS}^{CDCl_3}$ 1.40 (d, 3H), 3.53 (q, 1H), 3.95 (s, 2H), 6.90–7.70 (m, 6H), 8.10 (d, 1H), 9.77 ppm (s, 1H).

EXAMPLE 10

A stirred solution of 1 g. of 3-diazoacetyl-6,11-dihydrodibenzo-[b.e.]-thiepin-11-one (VII) in 100 ml. of chloroform is treated with 2 ml. of 47% aqueous hydriodic acid. After 1 hour at room temperature the reaction mixture is poured into 100 ml. of 3% aqueous sodium thiosulphate solution, the organic layer is separated and the aqueous layer is washed with 25 ml. of chloroform. The combined extract and washings are dried over magnesium sulfate, decolorized with charcoal and evaporated to dryness. Crystallization of the residue from ethanol affords 750 mg. of 3-acetyl-6,11-dihydrodibenzo-[b.e.]-thiepin-11-one (VIII), m.p. 139°–140° C.

EXAMPLE 11

500 Mg. of 3-acetyl-6,11-dihydrodibenzo-[b.e.]-thiepin-11-one, 675 mg. of methoxymethyltriphenylphosphonium chloride and 25 ml. of dry dimethoxyethane are placed in a dry flask, and the stirred reaction mixture is cooled to 0° C and treated with 4 ml. of a solution of potassium t-butoxide in t-butanol, (prepared by dissolving 1.48 g. of potassium in 40 ml. of t-butanol). The reaction mixture is allowed to warm to room temperature and after a further 20 minutes to reaction is quenched by the addition of 5 ml. of saturated aqueous ammonium chloride solution. The mixture is poured into 100 ml. of water and 25 ml. of benzene. The organic layer is separated and the aqueous layer is washed with 25 ml. of benzene. The combined organic layers are dried over magnesium sulfate and evaporated under reduced pressure, to yield a residue which is filtered through a column of 10 g. of silica gel, eluting with hexane:ethyl acetate (8:1). Evaporation of the eluate yields an oily product which crystallizes when triturated with ether:hexane (2 ml., 2:1), thus obtaining 275 mg. of 3-(2-methoxy-1-methyl)vinyl-6,11-dihydrodibenzo-[b.e.]-thiepin-11-one, (IX, $R^1$ = Me, mixture of cis and trans isomers), m.p. 110°–114° C.

Likewise, substituting ethoxymethyltriphenylphosphonium bromide and propoxymethyltriphenylphosphonium chloride for methoxymethyltriphenylphosphonium chloride there are respectively obtained 3-(2-ethoxy-1-methyl)vinyl-6,11-dihydrodibenzo-[b.e.]-thiepin-11-one and 3-(1-methyl-2-n-propoxy)vinyl-6,11-dihydrodibenzo-[b.e.]-thiepin-11-one.

EXAMPLE 12

A solution of 250 mg. of 3-(2-methoxy-1-methyl)vinyl-6,11-dihydrodibenzo-[b.e.]-thiepin-11-one in 10 ml. of toluene is dried by distilling off about 2 ml. of the solvent. The dry solution is treated with 1 drop of aqueous 70% perchloric acid and 1 ml. of dry methanol, and the reaction mixture is refluxed for 4 hours. It is then cooled and 2ml. of 10% aqueous sodium carbonate are added. The organic layer is separated, dried over magnesium sulfate and evaporated to dryness under reduced pressure. The oily residue is chromatographed on 5 g. of silica gel, using hexane:ethyl acetate (1:9) as eluant. Evaporation of the eluate yields 205 mg. of (dl) 3-(2,2-dimethoxy-1-methyl)ethyl-6,11-dihydrodibenzo-[b.e.]-thiepin-11-one (X, $R^1$ and $R^2$ = Me), a light brown oil, having the following physical constants: U.V.: $\lambda_{max}^{Diox}$ 248, 350 nm ($\epsilon$ 22,900, 3,200); I.R.: $\nu_{max}^{CHCl_3}$ 1640, 1600 cm$^{-1}$; N.M.R.:$\delta_{TMS}^{CDCl_3}$ 1.22 (d,3H), 2.93 (t, 1H), 3.20 (s, 3H), 3.30 (s, 3H), 3.96 (s, 2H), 4.24 (d, 1H), 6.90–7.60 (m, 6H), 8.00 ppm (d, 1H).

In a similar manner, substituting ethanol, n-propanol and n-butanol for methanol in the above procedure there are respectively obtained (dl) 3-(2-ethoxy-2-methoxy-1-methyl)ethyl-6,11-dihydrodibenzo-[b.e.]-thiepin-11-one, (dl) 31 -(2-methoxy-1-methyl-2n-propoxy)ethyl-6,11-dihydrodibenzo-[b.e.]-thiepin-11-one and (dl) 3-(2-n-butoxy-2-methoxy-1-methyl)ethyl-6,11-dihydrodibenzo-[b.e.]-thiepin-11-one, as pairs of diastereoisomers.

Likewise, using 3-(2-ethoxy-1-methyl)vinyl-6,11-dihydrodibenzo-[b.e.]-thiepin-11-one and 3-(1-methyl-2-n-propoxy)vinyl-6,11-dihydrodibenzo-[b.e.]-thiepin-11-one as starting materials and ethanol and propanol as reagents, respectively, there are obtained (dl) 3-(2-diethoxy-1-methyl)ethyl-6,11-dihydrodibenzo-[b.e.]-thiepin-11-one and (dl) 3-(2,2-di-n-propoxy-1-methyl)ethyl-6,11-dihydrodibenzo-[b.e.]-thiepin-11-one.

EXAMPLE 13

To a solution of 220 mg. of 3-(2-methoxy-1-methyl)-vinyl-6,11-dihydrodibenzo-[b.e.]-thiepin-11-one in 10 ml. of toluene there are added 1 ml. of ethylene glycol and 2 drops of 70% aqueous perchloric acid. distilling slowly 5 ml. of toluene from the reaction mixture to remove moisture. The solution is cooled, poured into 10 ml. of 10% aqueous sodium carbonate and extracted with benzene (2 × 20 ml). The combined extracts are dried over magnesium sulfate and evaporated to dryness under reduced pressure. The residue is chromatographed on 5 g. of silica gel, using hexane:ethyl acetate (9:1) as eluant. The eluate is evaporated to yeild an oil which is taken up in 5 ml. of ether, the cloudy section is filtered and the filtrate evaporated to yield 190 mg. of (dl) 2-[1-(6,11-dihydrodibenzo-[b.e.]-thiepin-11-one-3-yl)ethyl]-1,3-dioxolane (XI, Z = —CH$_2$—CH$_2$—), a pale yellow oil having the following physical constants: U.V.: $\lambda_{max}^{Diox}$ 248, 350 nm ($\epsilon$ 22,400, 2,600); I.R.: $\nu_{max}^{CHCl_3}$ 1640, 1600 cm$^{-1}$; N.M.R.: $\delta_{TMS}^{CDCl_3}$ 1.24 (d, 3H), 2.70–3.10 (m, 1H), 3.76 (s, 4H), 3.95 (s, 2H), 4.84 (d, 1H), 6.90–7.60 (m, 6H), 8.00 ppm (d, 1H);M.S.: m/e 326 (M+).

In a similar manner, substituting propylene glycol, 2,2-dimethylpropylene glycol and 2,3-dimethylbutan-1,4-diol for ethylene glycol there are respectively obtained:

(dl)  2-(6,11-dihydrodibenzo-[b.e.]-thiepin-11-one-3-yl) propionaldehyde propylene acetal,
(dl)  2-(6,11-dihydrodibenzo-[b.e.]-thiepin-11-one-3-yl) propionaldehyde 2,2-dimethylpropylene acetal and
(dl)  2-(6,11-dihydrodibenzo-[b.e.]-thiepin-11-one-3-yl) propionaldehyde 2,3-dimethylbutylene acetal.

EXAMPLE 14

A stirred mixture of 1.0 g. of 3-acetyl-6,11-dihydrodibenzo-[b.e.] thiepin-11-one (VIII). 1.4 g. of n-hexyloxymethyltriphenylphosphonium chloride and 25 ml. of dry dimethoxyethane is cooled to 0° C, and treated with 5.5 ml. of a solution of potassium t-butoxide in t-butanol (prepared by dissolving 0.57 g. of potassium in 20 ml. of dry t-butanol). After 5 minutes, the reaction mixture is treated with 0.5 ml. of acetic acid and then 100 ml. of saturated sodium chloride solution and 25 ml. of benzene are added. The organic layer is separated and the aqueous layer extracted with 25 ml. of benzene. The combined organic layers are dried over magnesium sulfate and evaporated to dryness under reduced pressure. Purification of the residue by column chromatography using 20 g. of silica gel and hexane:ethyl acetate (20:1) as eluant affords 990 mg. of 3-(2-n-hexyloxy-1-methyl)vinyl-6,11-dihydrodibenzo-[b.e.]-thiepin-11-one (IX, $R^1$ = n-C$_6$H$_{13}$), a pale yellow oil having the following physical constants: U.V. : $\lambda_{max}^{Diox}$ 245, 335 nm ($\epsilon$ 24000, 17800); I.R.: $\nu_{max}^{CHCl_3}$ 1640, 1585 cm$^{-1}$; N.M.R.: $\delta_{TMS}^{CDCl_3}$ 0.89 (t, 3H), 1.00– 1.80 (m, 8H), 1.90 (d, 3H), 3.65–4.00 (m, 2H), 3.97 (s, 2H), [6.18 (b.s), 6.53 (b.s)]1H, 6.90 – 7.60 (m, 6H), 7.94– 8.20 ppm. (2 × d, 1H).

EXAMPLE 15

To a solution of 520 mg. of 3-(2-n-hexyloxy-1-methyl)vinyl-6,11-dihydrodibenzo-[b.e.]-thiepin-11-one in 50 ml. of toluene there are added 2ml. of n-hexanol and one drop of 70% aqueous perchloric acid. The reaction mixture is heated to the boiling point and 25 ml. of toluene is distilled out of the reaction mixture over a 1 hour period. The cooled solution is treated with 1 ml. of 10% aqueous sodium carbonate and 50 ml. of water. The organic layer is separated, dried over magnesium sulfate and evaporated under reduced pressure. The oily residue is evaporated under high vacuum to remove excess of n-hexanol. The residue is carefully chromatographed on 5 g. of silica gel eluting with hexane: ethyl acetate (1:20, then 1:8), to yield 110 mg. of (dl) 3-(2,2-di-n-hexyloxy-1-methyl)ethyl-6,11-dihydrodibenzo-[b.e.]-thiepin-11-one (X, $R^1$ and $R^2$ = n-C$_6$H$_{13}$), as a pale yellow oil, having the following physical constants: U.V.: $\lambda_{max}^{Diox.}$ 250, 280, 350 nm ($\epsilon$ 24,000, 11,000, 2,900); I.R.:$\nu_{max}^{CHCl_3}$ 1645, 1600 cm$^{-1}$; N.M.R.:$\delta_{TMS}^{CDCl_3}$ 0.50–1.70 (m, 25H), 2.80–3.70 (m, 5H), 3.98 (s, 2H), 4.32 (d, 1H), 6.90–7.60 (m, 6H), 8.03 ppm (d, 1H).

What is claimed is:

1. A compound selected from the group of those represented by the formulas

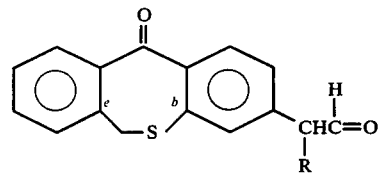 (A)

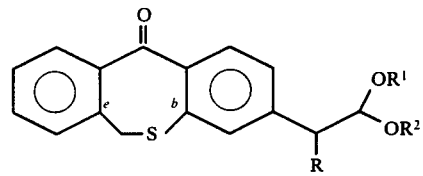 (B)

wherein R represents hydrogen or methyl, and each of $R^1$ and $R^2$, which can be the same or different, represents a lower alkyl group of 1 to 6 carbon atoms, or together represent a lower alkylene radical of 2 to 6 carbon atoms, provided that when R is methyl, the compounds are (dl) mixtures, and when $R^1$ and $R^2$ are different, the compounds are pairs of diasteroisomers and each diasteroisomeric isomer is a (dl) mixture.

2. The compound of claim 1, Formula (A), wherein R is hydrogen, 6,11-dihydrodibenzo-[b.e.]-thiepin-11-one-3-actaldehyde.

3. The compound of claim 1, Formula (A), wherein R is methyl, (dl) 2-(6,11-dihydrodibenzo-[b.e.]-thiepin-11-one-3-yl)propionaldehyde.

4. A compound of claim 1, Formula (B) wherein R is hydrogen and $R^1$ and $R^2$ are lower alkyl.

5. The compound of claim 4 wherein each $R^1$ and $R^2$ is methyl, 3-(2,2-diemthoxy)ethyl-6,11-dihydrodibenzo-[b.e.]-thiepin-11-one.

6. The compound of claim 4 wherein each $R^1$ and $R^2$ is n-hexyl, 3-(2,2-di-n-hexyloxy)ethyl-6,11-dihydrodibenzo-[b.e.]-thiepin-11-one.

7. A compound of claim 1 Formula (B) wherein R is hydrogen and $R^1$ and $R^2$ together are lower alkylene.

8. The compound of claim 7 wherein $R^1$ and $R^2$ together are ethylene, 2-[(6,11-dihydrodibenzo-[b.e.]-thiepin-11-one-3-yl)methyl]-1,3-dioxolane.

9. A (dl) compound of claim 1 Formula (B) wherein R is methyl and $R^1$ and $R^2$ are lower alkyl.

10. The (dl) compound of claim 9 wherein each $R^1$ and $R^2$ is methyl, (dl) 3-(2,2-dimethoxy-1-methyl) ethyl-6,11-dihydrodibenzo-[b.e.]-thiepin-11-one.

11. The (dl) compound of claim 9 wherein each $R^1$ and $R^2$ is n-hexyl, (dl) 3-(2,2-di-n-hexyloxy-1-methyl-)ethyl-6,11-dihydrodibenzo-[b.e.]-thiepin-11-one.

12. A (dl) compound of claim 1, Formula (B) wherein R is methyl and $R^1$ and $R^2$ together are lower alkylene.

13. The (dl) compound of claim 12 wherein $R^1$ and $R^2$ together are ethylene, (dl) 2-[1-(6,11-dihydrodibenzo-[b.e.]-thiepin-11-one-3-yl)ethyl]-1,3-dioxolane.

14. A compound of the formula:

(C)

wherein R is hydrogen or methyl and $R^1$ is a lower alkyl group of 1 to 6 carbon atoms.

15. The compound of claim 14 wherein R is hydrogen and $R^1$ is methyl, 3-(2-methoxy)vinyl-6,11-dihydrodibenzo-[b.e.]-thiepin-11-one.

16. The compound of claim 14 wherein R is hydrogen and $R^1$ is n-hexyl, 3-(2-n-hexyloxy)vinyl-6,11-dihydrodibenzo-[b.e.]-thiepin-11-one.

17. The compound of claim 14 wherein R and $R^1$ are methyl, 3-(2-methoxy-1-methyl)vinyl-6,11-dihydrodibenzo-[b.e.]-thiepin-11-one.

18. The compound of claim 14 wherein R is methyl and $R^1$ is n-hexyl, 3-(2-n-hexyloxy-1-methyl)vinyl-6,11-dihydrodibenzo-[b.e.]-thiepin-11-one.